(12) United States Patent
Hur et al.

(10) Patent No.: US 9,051,352 B2
(45) Date of Patent: Jun. 9, 2015

(54) METHOD FOR MANUFACTURING A GOLD CORE/INSULATOR SHELL NANOSTRUCTURE USING A NOVEL PEPTIDE

(75) Inventors: Hor-Gil Hur, Gwangju (KR); Jung Ok Kim, Gwangju (KR); Nosang Myung, Riverside, CA (US)

(73) Assignee: GWANGJU INSTITUTE OF SCIENCE AND TECHNOLOGY, Buk-Gu, Gwangju (KR)

( * ) Notice: Subject to any disclaimer, the term of this patent is extended or adjusted under 35 U.S.C. 154(b) by 162 days.

(21) Appl. No.: 13/643,233

(22) PCT Filed: Dec. 16, 2010

(86) PCT No.: PCT/KR2010/009012
§ 371 (c)(1),
(2), (4) Date: Oct. 24, 2012

(87) PCT Pub. No.: WO2011/136457
PCT Pub. Date: Nov. 3, 2011

(65) Prior Publication Data
US 2013/0243959 A1   Sep. 19, 2013

(30) Foreign Application Priority Data

Apr. 28, 2010   (KR) .................. 10-2010-0039521

(51) Int. Cl.
*C07K 7/08* (2006.01)
*B22F 1/02* (2006.01)
*B01J 13/18* (2006.01)
*B22F 1/00* (2006.01)
*B82Y 30/00* (2011.01)

(52) U.S. Cl.
CPC ... *C07K 7/08* (2013.01); *B22F 1/02* (2013.01); *B01J 13/18* (2013.01); *B22F 1/0018* (2013.01); *B22F 1/0025* (2013.01); *B22F 2001/0029* (2013.01); *B22F 2001/0033* (2013.01); *B22F 2001/0037* (2013.01); *B82Y 30/00* (2013.01)

(58) Field of Classification Search
USPC ....................................... 427/301
See application file for complete search history.

(56) References Cited

U.S. PATENT DOCUMENTS

| | | | | |
|---|---|---|---|---|
| 6,670,438 | B1 * | 12/2003 | Morse et al. | 528/21 |
| 7,335,717 | B2 * | 2/2008 | Morse et al. | 528/4 |
| 2010/0280220 | A1 * | 11/2010 | Hur et al. | 530/327 |

FOREIGN PATENT DOCUMENTS

| | | | |
|---|---|---|---|
| JP | 2009007616 | * | 1/2009 |
| JP | 2009126745 | * | 6/2009 |
| JP | 2010053385 | * | 3/2010 |

OTHER PUBLICATIONS

Kim et al, "Peptide directed synthesis of silica coated gold nanocables", ChemComm, (2010).*
The 2010 Autumn Conference on the Korean Society for Applied Biological Chemistry, Feb. 19, 2010, 3 pages.

* cited by examiner

*Primary Examiner* — Nathan T Leong
(74) *Attorney, Agent, or Firm* — Nath, Goldberg & Meyer; Joshua B. Goldberg; Sanjana Mangalagiri

(57) ABSTRACT

The present invention relates to a method for manufacturing a gold core/insulator shell nanostructure and a novel peptide used in the method. The method of the present invention is a biomimetic synthetic method using a silica-polymerizing peptide having a high affinity onto the surface of gold. The gold core/insulator shell nanostructure may be very effectively and environmentally friendly manner.

3 Claims, 5 Drawing Sheets

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Peptide for silica formation

<400> SEQUENCE: 1

Ser Ser Lys Lys Ser Gly Ser Tyr Ser Gly Ser Lys Gly Ser Lys Cys
1               5                   10                  15
```

METHOD FOR MANUFACTURING A GOLD CORE/INSULATOR SHELL NANOSTRUCTURE USING A NOVEL PEPTIDE

This is a National Phase Application filed under 35 U.S.C. 371 as a national stage of PCT/KR2010/009012, filed Dec. 16, 2010, and claiming the benefit from Korean Application No. 10-2010-0039521filed Apr. 28, 2010, the content of each of which is hereby incorporated by reference in its entirety.

TECHNICAL FIELD

The present invention disclosed herein relates to a method for manufacturing a gold core/insulator shell nanostructure using a novel peptide.

The Sequence Listing submitted in text format (.txt) filed on May 30, 2013, named "MBD_corrected_sequence_listing_05212013.txt", (created on May 21, 2013, (1KB), is incorporated herein by reference.

BACKGROUND ART

Recently, biological weaving techniques on multifunctional nanomaterials using biomimetic molecules such as DNA, proteins and peptides, attract much concern as environmentally friendly and diverse synthetic processes (1-2). The peptide is a specific amino acid sequence, and may selectively combine with a metal and may produce diverse nanomaterials by controlling the size, the shape, the crystal structure and the function thereof (3-5). In view of the specificity and the diversity, the peptides receive the greatest attention among the above-described bio molecules.

The peptides may be used as a reducing agent or a capping agent for synthesizing silver nanoparticles, calcium molybdate fluorescent microparticles, gold nanoparticles, meta titanic acid precipitates, titania nanoparticles, etc. (6-11). In addition, the peptides may be possibly applied as a building block of nanomaterials such as peptide nanotubes, nanospheres and nanorings through a self-assembly (12-16).

A synthetic method of one-dimensional nanostructures such as a wire, a rod, a tube and a ribbon has been received attention because of the high ratio of surface area to volume, and specific electrical, optical and catalytic properties of the one-dimensional nanostructures (17-19). In addition, different from uniformly organized nanomaterials, a one-dimensional nanocable structure has a high stability and increased chemical and physical properties, and so is appropriately applied as an electronic device and a sensor (20-21). Synthetic methods of the nanocable structure may be classified into three categories of a template covering method, a template filling method and a simultaneous synthesis method. The template covering method is a technique of coating nanowire or nanorod cores with other materials such as a metal, a metal oxide and a polymer by using chemical, electrochemical or physical vapor processes or a synthetic process (22-24). The template filling method is a technique of filling a metallic material such as gold, silver and cobalt in peptide or polymer nanotubes used as a template (25-27). In addition, synthetic methods of manufacturing a nanocable structure such as silver/polypyrrole and copper/polyvinyl alcohol are known as a one step simultaneous synthesis method (28-29).

A plurality of theses and patent literatures are referenced in the whole specification of the present application, and the references are herein listed. The cited theses and patent literatures are wholly included as the references in the specification of the present application, in order to more precisely describe the technical field of the present application and the content of the present inventive concept.

DISCLOSURE

Technical Problem

The inventors of the present invention made efforts to develop a biological method of manufacturing a multifunctional nanomaterial and manufactured a gold core/insulator shell nanostructure using a novel peptide to complete the present invention.

Therefore, an object of the present invention is to provide a method for manufacturing a gold core/insulator shell nanostructure using a novel peptide.

Another object of the present invention is to provide the novel peptide.

The other objects and advantages of the present invention will be more apparent through the following detailed description of the invention, claims and drawings described hereinafter.

Technical Solution

In accordance with an exemplary embodiment of the present invention, a method for manufacturing a gold core/insulator shell nanostructure is provided. The method includes (a) combining a silica-polymerizing peptide including a cysteine residual group with a surface of a gold nanostructure; and (b) forming the gold core/insulator shell nanostructure through a reaction of the peptide combined with the surface of the gold nanostructure with a silica precursor represented by the following Chemical Formula 1.

$$R_{1n}Si(OR_2)_{4-n} \quad \text{Chemical Formula 1}$$

In Chemical Formula 1, each of $R_1$ independently represents a hydrogen atom, a straight or branched alkyl group having 1 to 6 carbon atoms, a vinyl group or a phenyl group, each of $R_2$ independently represents a straight or branched alkyl group having 1 to 6 carbon atoms, and n represents an integer of 0 to 3.

The step (a) in example embodiments is a step of combining the silica-polymerizing peptide including a cysteine residual group at the terminal portion thereof with the surface of the gold nanostructure by using the cysteine residual group at the terminal portion. Cysteine is an amino acid including a thiol group capable of forming a covalent bond with the surface of the gold, and so may combine with the surface of the gold through the thiol group.

It could be confirmed by the present inventors that when the silica-polymerizing peptide having the cysteine residual group at the terminal portion is combined with the surface of the gold nanostructure, and then is reacted with the silica precursor by using the thiol group, silica may be effectively precipitated on the surface of the gold nanostructure. However, when the silica-polymerizing peptide having no cysteine residual group at the terminal portion is used, a silica layer was not formed on the surface of the gold nanostructure.

The silica-polymerizing peptide having the cysteine residual group at the terminal portion in accordance with example embodiments, represents a peptide including at least one cysteine residual group at the N-terminal or C-terminal portion thereof among known silica-polymerizing peptides in this art, or a peptide including at least one additional cysteine residual group at the N-terminal or C-terminal portion of well known silica-polymerizing peptides. The manufacturing method in accordance with example embodiments has a feature in that a silica synthesis process is performed at a combined state of a silica-polymerizing peptide with the surface of gold by using a thiol group of terminal cysteine, and silica is precipitated at the surface of a gold nanostructure. Accordingly, the silica-polymerizing peptide having the cysteine residual group at the terminal portion in the range of the present inventive concept includes all the silica-polymerizing peptides capable of precipitating the silica on the surface of the gold nanostructure by using the thiol group of the terminal cysteine at the combined state of the silica-polymerizing peptide with the surface of the gold, including known peptides along with novel silica-polymerizing peptides to be reported in the future.

The silica-polymerizing peptides utilizable in the example embodiments has been reported in various literatures in detail (U.S. Pat. No. 6,670,438; Wolf S. E. et al., Formation of silicones mediated by the sponge enzyme silicatein-alpha, Dalton Trans, Epub ahead of print(2010); Schr H. C. et al., Silicatein: nanobiotechnological and biomedical applications, Prog Mol Subcell Biol., 47:251-73(2009); Shimizu Shimizu K. et al., Silicatein alpha: cathepsin L-like protein in sponge biosilica., Proc Natl Acad Sci USA., May 26; 95(11): 6234-8(1998)). The silica-polymerizing peptides excluding the terminal cysteine residual group among the silica-polymerizing peptides described in the above literatures may be used in example embodiments as an added type of one or more cysteine residual groups at the N-terminal or C-terminal of the peptides.

In accordance with an embodiment of the present inventive concept, the silica-polymerizing peptide including the cysteine residual group at the terminal portion may be silication subunit alpha, silication subunit beta, silication subunit gamma, poly(L-cysteine 10-b-L-lycine 200), poly(L-cysteine 30-b-L-lycine 200), poly(L-cysteine 60-b-L-lycine 200), poly(L-cysteine 30-b-L-lycine 400) or peptide Si#6-C.

In accordance with a preferred embodiment of the present inventive concept, the silica-polymerizing peptide having the cysteine residual group at the terminal portion includes peptide Si#6-C. Peptide Si#6-C is a peptide including the cysteine at the C-terminal thereof and capable of manufacturing silica nanoparticles from a silica precursor. The amino acid sequence of the peptide Si#6-C is SSKKSGSYSGSKGSKC (first sequence in a sequence list).

In accordance with a preferred embodiment of the present inventive concept, the step (a) for attaching the peptide onto the gold nanostructure is performed at room temperature for 1 to 48 hours, and the peptide uncombined with the surface of the gold nanostructure may be easily removed through various known methods in this art including a centrifugal separation, etc.

The gold nanostructure used in the step (a) in accordance with example embodiments may include diverse shapes of the gold nanostructures without limitation. For example, a gold nanoribbon, a gold nanoplatelet, a gold nanotube, a gold nanowire, a gold nanorod, a gold nanoparticle, a gold nanocage, a gold nanocomposite, a gold nanoflake, a gold nanoflower, a gold nanofoam, a gold nanomesh, a gold nanofiller, a gold nanopin film, a gold nanoring or a gold nanoshell, may be used.

The step (b) in accordance with example embodiments is a step of forming the gold core/insulator shell nanostructure through a reaction of the peptide combined with the surface of the gold nanostructure with the silica precursor. The silica precursor is represented by the following Chemical Formula 1.

$$R_{1n}Si(OR_2)_{4-n} \quad \text{Chemical Formula 1}$$

In Chemical Formula 1, each of $R_1$ independently represents a hydrogen atom, a straight or branched alkyl group having 1 to 6 carbon atoms, a vinyl group or a phenyl group, each of $R_2$ independently represents a straight or branched alkyl group having 1 to 6 carbon atoms, and n represents an integer of 0 to 3.

In Chemical Formula 1, examples of four functional alkoxysilanes represented by $Si(OR_2)_4$ when n is 0, include tetramethoxysilane, tetraethoxysilane, tetra-n-propoxysilane, tetra-iso-propoxysilane, tetra-n-butoxysilane, tetra-sec-butoxysilane, tetra-tert-butoxysilane, etc.

In Chemical Formula 1, examples of three functional alkoxysilanes represented by $R_1Si(OR_2)_3$ when n is 1, include trimethoxysilane, triethoxysilane, methyl trimethoxysilane, methyl triethoxysilane, ethyl trimethoxysilane, ethyl triethoxysilane, propyl trimethoxysilane, propyl triethoxysilane, isobutyl triethoxysilane, cyclohexyl trimethoxysilane, phenyl trimethoxysilane, phenyl triethoxysilane, vinyl trimethoxysilane, vinyl triethoxysilane, allyl trimethoxysilane, allyl triethoxysilane, methyl tri-n-propoxysilane, methyl tri-isopropoxysilane, methyl tri-n-butoxysilane, methyl tri-sec-butoxysilane, methyl tri-tert-butoxysilane, ethyl tri-n-propoxysilane, ethyl triisopropoxysilane, ethyl tri-n-butoxysilane, ethyl tri-sec-butoxysilane, ethyl tri-tert-butoxysilane, n-propyl tri-n-propoxysilane, n-propyl triisopropoxysilane, n-propyl tri-n-butoxysilane, n-propyl tri-sec-butoxysilane, n-propyl tri-tert-butoxysilane, iso-propyl trimethoxysilane, iso-propyl triethoxysilane, iso-propyl tri-n-propoxysilane, iso-propyl triisopropoxysilane, iso-propyl tri-n-butoxysilane, iso-propyl tri-sec-butoxysilane, iso-propyl tri-tert-butoxysilane, n-butyl trimethoxysilane, n-butyl triethoxysilane, n-butyl tri-n-propoxysilane, n-butyl triisopropoxysilane, n-butyl tri-n-butoxysilane, n-butyl tri-sec-buthoxysilane, n-butyl tri-tert-butoxysilane, n-butyl triphenoxysilane, sec-butyl trimethoxysilane, sec-butyl-tri-n-propoxysilane, sec-butyl tri-iso-propoxysilane, sec-butyl tri-sec-butoxysilane, sec-butyl tri-tert-butoxysilane, tert-butyl trimethoxysilane, tert-butyl triethoxysilane, tert-butyl tri-n-propoxysilane, tert-butyl triisopropoxysilane, tert-butyl tri-n-butoxysilane, tert-butyl tri-sec-butoxysilane, tert-butyl tri-tert-butoxysilane, phenyl tri-n-propoxysilane, phenyl triisopropoxysilane, phenyl tri-n-butoxysilane, phenyl tri-sec-butoxysilane and phenyl tri-tert-butoxysilane.

In Chemical Formula 1, examples of two functional alkoxysilanes represented by $(R_1)_2Si(OR_2)_2$ when n is 2, include dimethyl dimethoxysilane, dimethyl diethoxysilane, diphenyl dimethoxysilane, diphenyl diethoxysilane, diethyl dimethoxysilane, diethyl diethoxysilane, methyl ethyl dimethoxysilane, methyl ethyl diethoxysilane, methyl phenyl dimethoxysilane, methyl phenyl diethoxysilane, ethyl phenyl dimethoxysilane and ethyl phenyl ethoxysilane.

In Chemical Formula 1, alkoxysilanes when n is 2, i.e., represented by $(R_1)_2Si(OR_2)_2$, are referred to alkoxysilanes having two functional groups. In Chemical Formula 1, alkoxysilanes when n is 3, i.e., represented by $(R_1)_3Si(OR_2)$, are referred to alkoxysilanes having one functional group.

In Chemical Formula 1, examples of one functional alkoxysilanes represented by $(R_1)_3Si(OR_2)$ when n is 2, include trimethyl methoxysilane, trimethyl ethoxysilane, triphenyl methoxysilane, triphenyl ethoxysilane, methyl diethoxysilane, dimethyl vinyl methoxysilane, dimethyl vinyl ethoxysilane, phenyl dimethyl methoxysilane, phenyl dimethyl ethoxysilane, diphenyl methyl methoxysilane and diphenyl methyl ethoxysilane.

In a preferred embodiment according to the present inventive concept, the silica precursor is selected from the group consisting of tetramethoxysilane, tetraethoxysilane, trimethoxysilane, triethoxysilane, methyl trimethoxysilane, methyl triethoxysilane, dimethyl dimethoxysilane and dimethyl diethoxysilane.

In accordance with an embodiment of the present inventive concept, the step (b) may be performed by adding the peptide combined with the surface of the gold nanostructure into a solution including the silica precursor and then conducting a reaction for from 10 minutes to 10 hours.

In accordance with another example embodiment of the present invention, a novel peptide includes an amino acid sequence represented by the first sequence in the sequence list.

The novel peptide in accordance with example embodiments is a peptide having cysteine combined at the C-terminal of peptide Si#6 and possibly producing silica nanoparticles from the silica precursor. The novel peptide has a dual function including a function of forming the silica nanoparticles and a function of combining the peptide with the surface of the gold through the thiol group in the terminal cysteine.

The novel peptide in accordance with example embodiments is a silica-polymerizing peptide having an amino acid sequence represented by the first sequence in a sequence list and including a cysteine residual group at the terminal portion thereof Silica may be precipitated on the surface of the gold nanostructure while the silica-polymerizing peptide being attached to the surface of the gold by using the thiol group of the terminal cysteine. Thus, the novel peptide may be used for manufacturing a gold core/insulator shell nanostructure. Since the novel peptide in accordance with example embodiments is the silica-polymerizing peptide including the cysteine residual group at the terminal portion, and may be used in the method for manufacturing the gold core/insulator shell nanostructure, the common description with the description concerning the method for manufacturing may be omitted to avoid an excessive complexity.

According to an embodiment of the present inventive concept, the gold core/insulator shell nanostructure is a gold/insulator coaxial nanocable. The gold/insulator coaxial nanocable may be manufactured by using a gold nanoribbon as the gold nanostructure. Particularly, the novel peptide in accordance with example embodiments may be combined with the gold nanoribbon, and then reacting the peptide combined gold nanoribbon with a solution including the silica precursor.

Advantageous Effects

The features and advantages of the example embodiments will be summarized as follows:

(i) A method for manufacturing a gold core/insulator shell nanostructure and a novel peptide used in the method are provided.

(ii) Since the method in accordance with example embodiments is a biomimetic synthetic method using a silica-polymerizing peptide having a high affinity with the surface of the gold, a gold core/insulator shell nanostructure may be manufactured in an effective and environmentally friendly manner.

BEST MODE

Figure 1:
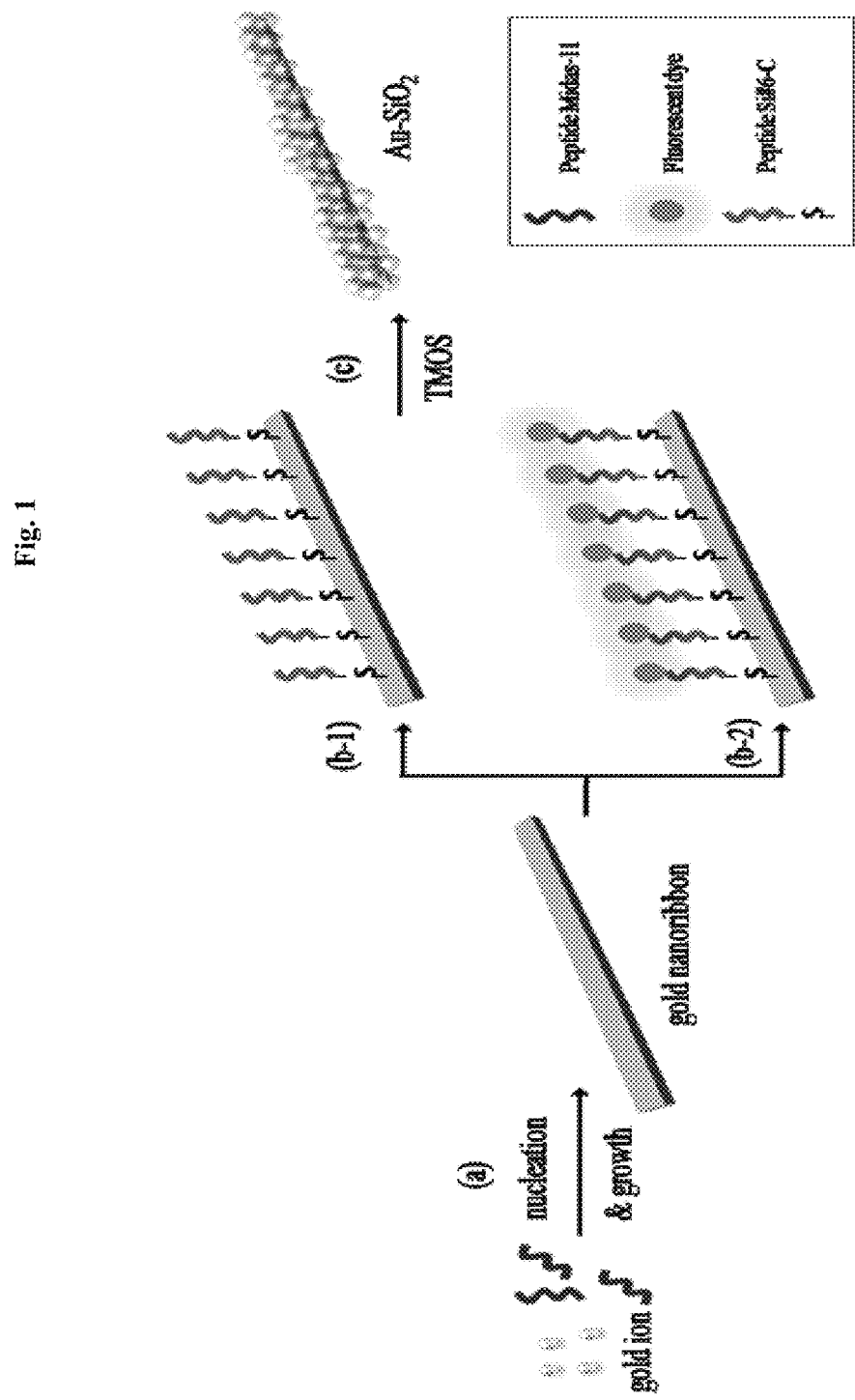
FIG. 1 is a schematic diagram for explaining a method for manufacturing a gold/silica nanocable in which (a) represents synthesis of a gold nanoribbon using peptide Midas-11, (b-1) represents attachment onto the surface of gold by using a thiol group of newly designed peptide Si#6-C, (b-2) represents binding affinity onto the surface of gold of fluorescent dye indicated peptide FAM-Si#6-C, and (c) represents synthesis of a nanocable by coating the surface of gold with TMOS derived silica.

Hereinafter, the present invention will be described in detail with reference through example embodiments. The example embodiments are provided only for describing the present invention more particularly, and the scope of the present invention according to the gist of the present invention should not be construed as limited to the embodiments set forth herein to those skilled in the art.

Example Embodiments

Experimental Materials and Procedures

1. Chemicals and Peptides $HAuCl_4 \cdot 3H_2O$ and TMOS were purchased from Aldrich (St. Louis, Mo.). Nanopure water was prepared by using Milli-Q system (Millipore, Billerica, Mass.) and was autoclaved to avoid microbial contamination. All peptides used were purchased from AnyGen Co., Ltd. (Gwangju, Korea).

2. Synthesis of Gold Nanoribbons and Nanoplatelets

All the procedures for synthesizing gold nanoribbons and nanoplatelets were followed the previous description in the reference literature (5). The gold nanoribbons were synthesized by using 0.2 mg/Ml of peptide Midas-11 dissolved in de-ionized water at pH 5.4 and including 30 mM of $HAuCl_4$, and by performing a reaction at 37° C. for three days in a dark room. Initial pH condition of the de-ionized water including $HAuCl_4$ was adjusted using 5 M NaOH prior to adding the peptide solution. The gold nanoplatelets were synthesized by using 0.2 mg/Ml of the peptide Midas-11 dissolved in de-ionized water at pH 3.0 and including 0.5 mM of $HAuCl_4$, and by performing a reaction at 37° C. for three days in a dark room. All reaction volume was 1 Ml. After the reaction, samples were centrifuged and then washed twice using de-ionized water.

3. Attaching Peptides onto Gold Nanostructures

A reaction of each template of the gold nanoribbon (50 Ml) and the gold nanoplatelet (10 Ml) synthesized from the solution with 1 mg of Si#6-C peptide was carried out for 24 hours at room temperature. After 24 hours, a centrifugal separation (Centrifuge 5415D, Eppendorf, Fisher Scientific, Pittsburgh, Pa.) was performed at 10,000 rpm for 5 minutes, and supernatants including un-reacted Si#6-C peptide were discarded.

4. Coating the Gold Nanostructures with Silica

A reaction of each of the gold nanoribbon and the gold nanoplatelet combined with Si#6-C peptide with 50 mM of TMOS was carried out in a 50 mM phosphate buffer solution (pH 7.5) at 20° C. for 3 hours to form a silica layer. A TMOS stock solution was freshly prepared as 1 M concentration solution by dissolving in 1 mM HCl. After reaction, thus obtained samples were washed twice by using de-ionized water and were resuspended in de-ionized water for further analysis.

5. Evaluating Binding Affinity of Fluorescent Dye-Labeled Si#6-C Peptide

A reaction of the synthesized gold nanoribbon with 1 mg of FAM-Si#6 or FAM-Si#6-C was carried out for 24 hours at room temperature. After completing the reaction, thus obtained sample was centrifuged and washed twice using de-ionized water. Light intensity of the binding affinity of the designed peptides was compared and analyzed using CLSM.

6. Characterization of Materials

The characteristics of the synthesized nanocables and nanoplatelets were analyzed by means of SEM, FE-TEM, EDX and AFM. 5 μl of a suspension was placed on a wafer and then was dried to prepare a sample for SEM analysis. A secondary SEM image was taken using Hitachi S-4700 (Tokyo, Japan) and an accelerating voltage was fixed to 10 kV. AFM analysis was also conducted using the SEM sample. An AFM image was taken using NanoMan D-3100 (Veeco, Plainview, N.Y.). TEM analysis was conducted using JEM 2100F FE-TEM (JEOL, Peabody, Mass.) equipped with EDX at an accelerating voltage of 300 kV. A sample was prepared by dropping one drop of a suspension of a gold crystal on a carbon-coated Cu supporting grid, and then drying in the air.

Experimental Results

Peptides for gold-synthesis, Midas-11 and Midas-11C, were derived from Midas-2 peptide sorted from a combination type phage display peptide library, and the eleventh amino acid of the Midas-2 peptide, tyrosine, was substituted by glycine and cysteine, respectively (5). Peptide Si#6 (31) is found in a diatom, and is derived from R5 (30) well known as a peptide for synthesizing silica. Peptide Si#6 is a mutant lacking of C-terminal amino acid, RRIL, of R5 and may produce silica nanoparticles of 85 to 130 nm. The novel peptide Si#6-C in accordance with example embodiments was designed to have two functions simultaneously. That is, the novel peptide may form silica nanoparticles and include cysteine having a thiol group for making a covalent bond with the surface of gold at the C-terminal portion so as to be attached onto the surface of the gold by using the thiol group. In order to compare and evaluate the binding affinity of the peptide Si#6-C in accordance with example embodiments with the surface of the gold nanoribbon with respect to that of the common peptide Si#6, peptides of which N-terminals were labeled by NHS-fluorescein, i.e. FAM-Si#6-C and FAM-Si#6 were designed, and evaluation on the binding affinity was conducted. Designed peptides for manufacturing gold/silica nanocables and amino acid sequences thereof are illustrated in the following Table 1.

TABLE 1

| Peptides | Sequences | References |
|---|---|---|
| Peptides for forming silica | | |
| R5 | SSKKSGSYSGSKGSK*RRIL* | 30 |
| Si#6 | SSKKSGSYSGSKGSK | 31 |
| Si#6-C | SSKKSGSYSGSKGS*KC* | Present application |
| [a]FAM-Si#6 | FAM-SSKKSGSYSGSKGSK | Present application |
| FAM-Si#6-C | FAM-SSKKSGSYSGSKGS*KC* | Present application |

TABLE 1-continued

| Peptides | Sequences | References |
|---|---|---|
| Peptides for forming gold nanostructure | | |
| Midas-2 | TGTSVLIATP*Y*V | 5 |
| Midas-11 | TGTSVLIATP*G*V | 5 |
| Midas-11C | TGTSVLIATP*C*V | 5 |

[a]FAM is an abbreviation of fluorescent dye NHS-fluorescein.

Figure 2:
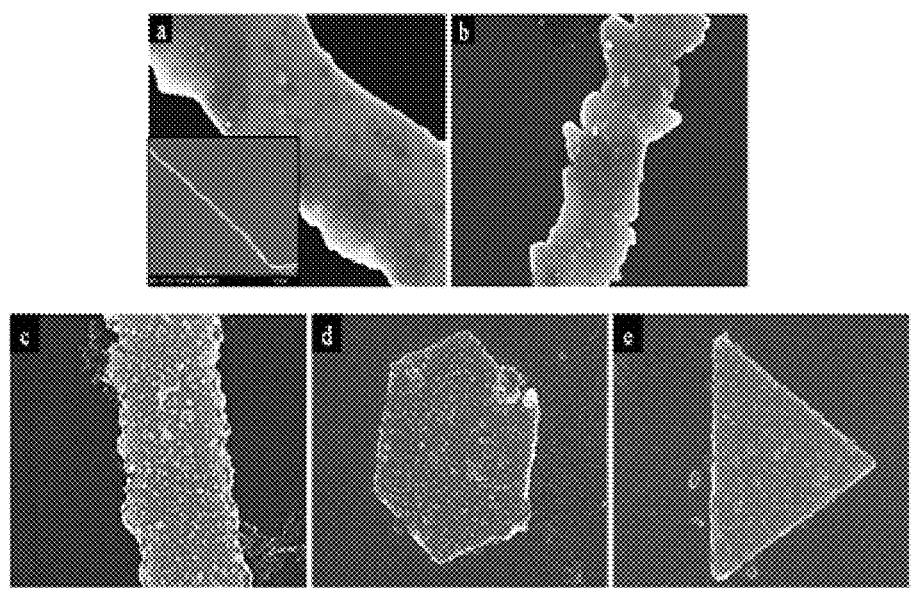
FIG. 2 illustrates SEM images of nanostructures synthesized from peptides in which (a) corresponds to a gold nanoribbon prior to coating, synthesized by using peptide Midas-11, (b) corresponds to an uncoated gold nanoribbon after reacting with TMOS precursor without peptide Si#6-C, (c) corresponds to a gold/silica nanocable synthesized by using 1 mg of peptide Si#6-C and 50 mM of TMOS, and (d) and (e) respectively correspond to hexagonal and triangle gold/silica nanoplatelets synthesized by using 1 mg of peptide Si#6-C and 50 mM of TMOS.

A total experimental process for synthesizing a gold/silica coaxial nanocable structure using the peptides designed as above is illustrated in FIG. 1. The first step for synthesizing the gold/silica coaxial nanocable includes performing a reaction in a solution having the pH of 5.4 and including 30 mM of HAuCl$_4$ at 37° C. for three days in a dark room to synthesize gold nanoribbons using peptide Midas-11, as described in a reference literature (5). The smooth surface of thus synthesized gold nanoribbon was observed by means of a scanning electron microscope (SEM) (FIG. 2A). The length of the gold nanoribbon was several tens micrometers (see inserted drawing in FIG. 2A). The gold nanoribbon may function as a core for precipitating silica while manufacturing a gold/silica coaxial nanocable structure. As the second step, the double functional peptide Si#6-C and the synthesized gold nanoribbon were reacted at room temperature for 24 hours. After 24 hours, the reactant was centrifuged at 10,000 rpm for 5 minutes and un-reacted peptide Si#6-C was discarded. After that, thus obtained product was reacted with 50 mM tetramethylorthosilicate (TMOS) precursor at 20° C. for 3 hours to coat the gold nanoribbon through peptide Si#6-C attached on the surface of the gold with amorphous silica. Different from the smooth surface of the gold nanoribbon before the coating, the rough surface of the gold nanoribbon and the silica thin film formed on the surface may be confirmed in FIG. 2C. In order to evaluate the synthesis of the silica layer on the surface of the gold without using Si#6-C peptide, 50 mM of TMOS precursor was directly reacted with the gold nanoribbon at 20° C. for 3 hours, as a control experiment. From the result of the control experiment, it was confirmed that no distinct silicon layer was formed on the surface of the gold nanoribbon (FIG. 2B). From the result, the Si#6-C peptide having the dual functions of making a bonding with the surface of the gold is acknowledged to become a decisive factor in coating the surface of the gold nanoribbon with silica and constructing a gold/silica nanocable structure.

Besides the experiment on the gold nanoribbon, experiments on hexagonal and triangle gold nanoplatelets synthesized by performing a reaction with 30 mM of HAuCl$_4$ at the pH of 3.0 at 37° C. for three days in a dark room from the peptide Midas-11, were conducted to confirm if the system in accordance with the present inventive concept of coating the nanostructure may be applied to the gold structure of different dimensions (FIGS. 2D and 2E). From the result, the Si#6-C peptide in accordance with example embodiments was confirmed to have a property of accumulating silica on the surface of the hexagonal and triangle gold nanoplatelets.

Figure 3:
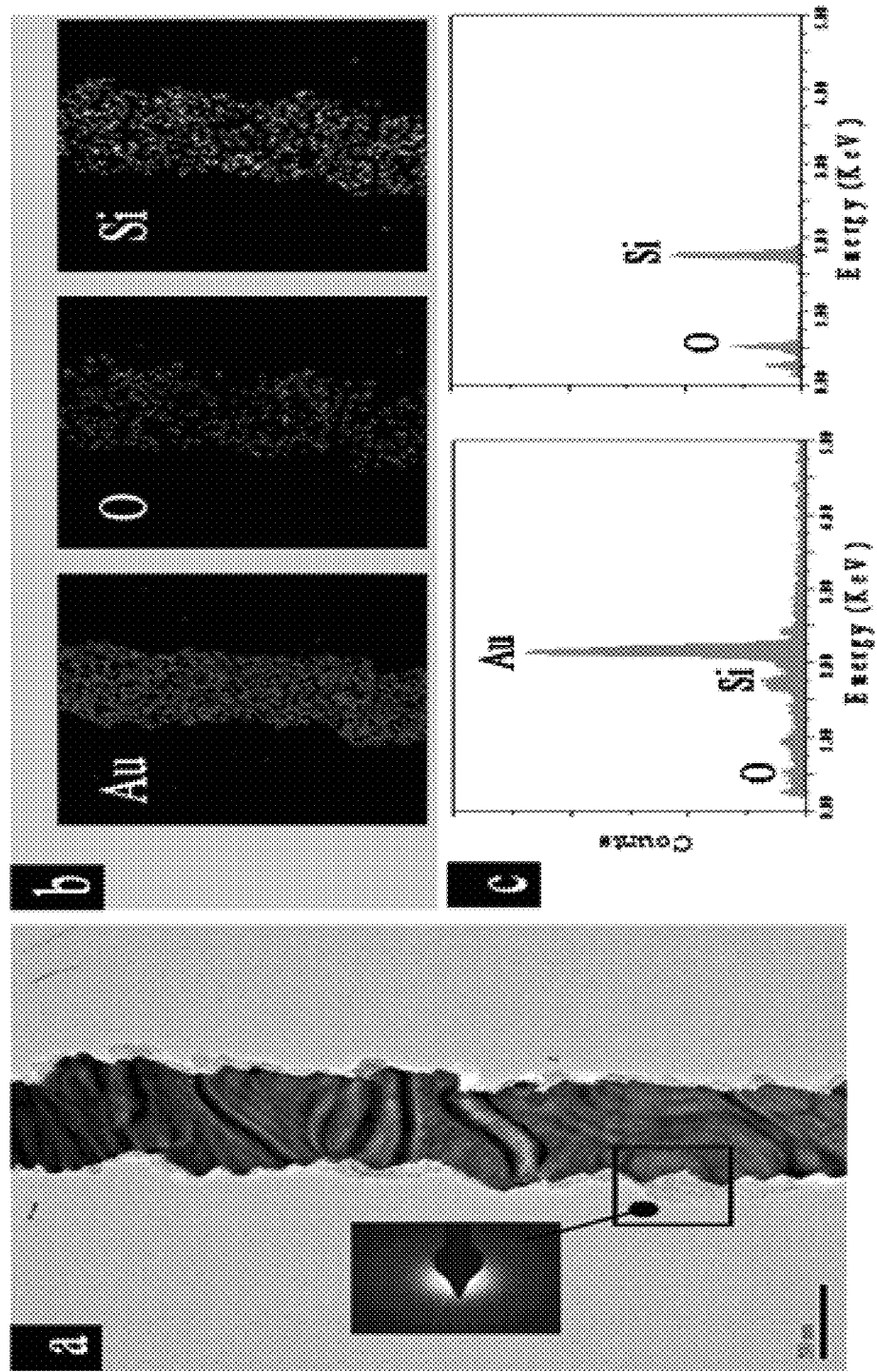
FIG. 3 illustrates (a) a TEM image of a gold/silica nanocable synthesized by using 1 mg of peptide Si#6-C and 50 mM of TMOS, (b) EDX mappings of gold, oxygen and silicon, respectively, and (c) EDX analysis results on gold/silica nanocable and silica portions.
Figure 4:
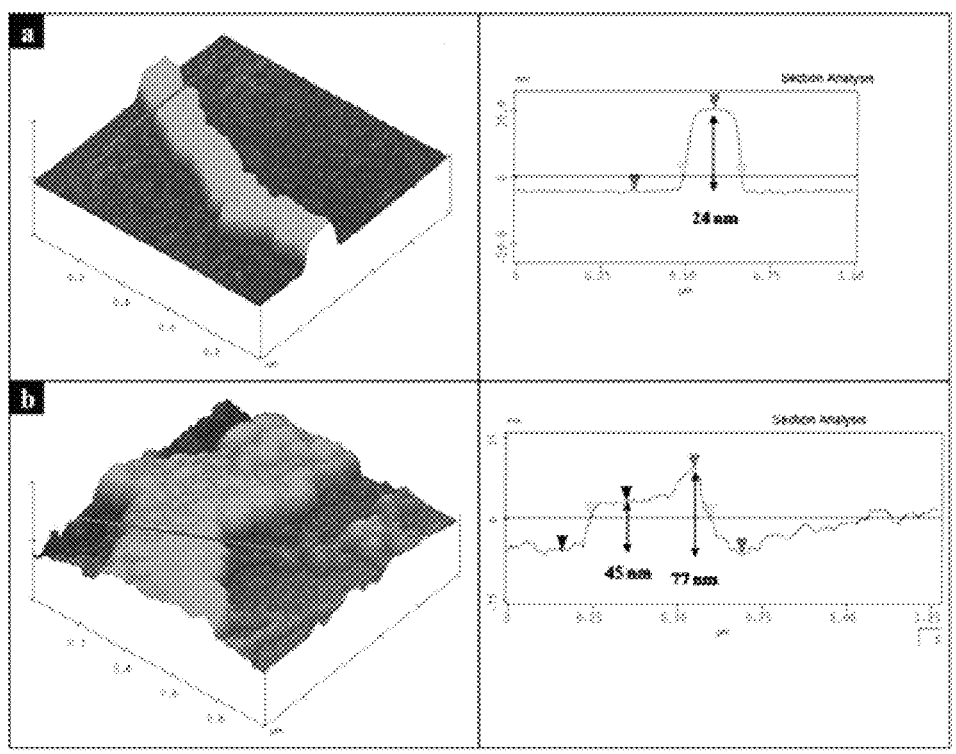
FIG. 4 illustrates (a) AFM images of an uncoated gold nanoribbon, and (b) AFM images of a gold/silica nanocable synthesized by using 1 mg of peptide Si#6-C and 50 mM of TMOS.

According to a transmission electron microscope (TEM) image conducted on a silica layer coated on the gold core by using the above-designed peptides, an amorphous silica layer was shown (FIG. 3A and inserted drawing). In addition, from the element mappings and point analyses of the energy dispersive x-ray spectroscopy (EDX), the formation of a thin silica layer completely covering the surface of the mold core and the gold may be confirmed (FIGS. 3B and 3C). Further, atomic force microscope (AFM) analyses were conducted with respect to gold core/silica coated coaxial nanocable structures obtained from the reaction of the uncoated gold nanoribbon with 50 mM of TMOS. The untreated gold nanoribbon had an even and uniform surface of a height of about 24 nm, however, the gold core/silica coated coaxial nanocable structure had a thicker and rough surface of a height of about 45-77 nm.

The binding affinities with respect to the surfaces of the gold nanoribbons of the peptide Si#6-C including cysteine and Si#6 excluding cysteine were compared. The N-terminals of the peptides were labeled by green light emitting fluorescent dye NHS-fluorescein (FAM) to obtain FAM-Si#6-C and FAM-Si#6. 1 mg of FAM-Si#6-C and FAM-Si#6 were reacted with the gold nanoribbons at room temperature for 24 hours in a dark room. Then, the reactant was centrifuged at 10,000 rpm for 5 minutes, and un-reacted peptides were discarded.

Figure 5:
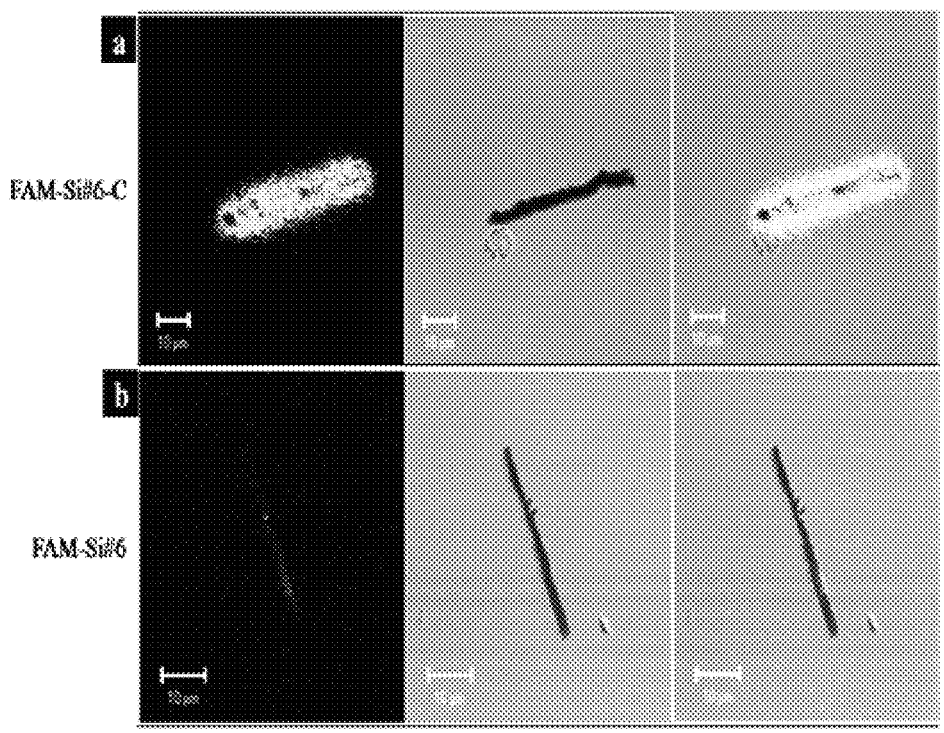
FIG. 5 illustrates (a) CLSM images of gold nanoribbons combined with fluorescent dye-labeled peptide FAM-Si#6-C and (b) CLSM images of gold nanoribbons combined with FAM-Si#6, after reacting for 24 hours.

The light intensity emitted from the fluorescent dye-labeled peptides specifically combined with the surface of the gold nanoribbon was measured by a confocal laser scanning microscope (CLSM) (FIG. 5). However, the gold nanoribbon reacted with the peptide FAM-Si#6-C emitted a strong fluorescent light to confirm the specifically combined peptide onto the surface of the gold nanoribbon (FIG. 5A). However, the gold nanoribbon reacted with the peptide FAM-Si#6 emitted weak and non-uniformly dispersed fluorescent light, implying that the peptide was not specifically combined with the surface of the gold nanoribbon (FIG. 5B). From the result, it could be found that the bonding of one cysteine at the C-terminal of the silica-polymerizing peptide was necessary and sufficient to form a covalent bond at the gold nanostructure. The formation of the silica thin film on the gold nanostructure was acknowledged not to be disturbed by the cysteine bonding. Most of the methods for synthesizing one dimensional nanocable conducted until now have been chemical or physical methods. In addition, in order to synthesize the gold core/silica shell nanocable, only limited researches have been conducted (34). Researches on methods for biomimetically synthesizing a nanocable by coating gold nanoribbons with silica using bio molecules such as newly designed peptides, have not been conducted. In addition, the total process for constructing a nanomaterial complex such as a core/shell nanocable may be controlled according to a biological weaving method in an environmental condition of synthesizing gold nanoribbons and forming a silica layer of a gold/silica nanocable.

In conclusion, a constructing method of a coaxial nanocable structure by coating gold nanoribbons synthesized by using two newly designed peptides with silica, is provided in accordance with example embodiments. One of the peptides is for synthesizing a gold nanostructure and the other is for making a bond with the gold nanostructure irrespective of the shapes of the core template and forming a silica layer. One thiol group included in the C-terminal cysteine of Si#6-C peptide is sufficient for forming a strong bonding with the gold nanostructure and does not prevent the specific formation of a layer of amorphous silica nanoparticles onto the gold nanostructure. In addition, the silica layer on the surface of the gold nanoribbon may be controlled by changing the concentration of a reacting silica precursor. The method for synthesizing the metal/insulator coaxial nanocable structure by coating the gold nanoribbon with silica by using the newly designed peptides in accordance with the present inventive concept, is an embodiment showing the application possibility of bio molecules which may diversely change for another appropriate object in constructing well-designed multifunctional nanostructure.

As described above, specific parts of the present invention have been described in detail, however, are intended to illustrate only preferred embodiments for a person skilled in the art. Thus, the scope of the present invention is to be determined by the broadest permissible interpretation of the following claims and their equivalents, and shall not be restricted or limited by the foregoing detailed description.

REFERENCES

1. Ehud, G. *FEBS J.* 2007, 274, (2), 317-322.
2. Sotiropoulou, S.; Sierra-Sastre, Y.; Mark, S. S.; Batt, C. A. *Chem. Mat.* 2008, 20, (3), 821-834.
3. Dickerson, M. B.; Sandhage, K. H.; Naik, R. R. *Chem. Rev.* 2008, 108, (11), 4935-4978.
4. Tamerler, C.; Sarikaya, M. *Philos. Trans. R. Soc. A-Math. Phys. Eng. Sci.* 2009, 367, (1894), 1705-1726.
5. Kim, J. Rheem, Y. Yoo, B. Chong, Y. Bozhilov, K. N. Kim, D. Sadowsky, M. J. Hur, H. -G. Myung, N. V. *Acta Biomater.* 2010, in press.
6. Naik, R. R.; Stringer, S. J.; Agarwal, G.; Jones, S. E.; Stone, M. O. *Nat. Mater.* 2002, 1, 169-172.
7. Sarikaya, M.; Tamerler, C.; Jen, A. K.-Y.; Schulten, K.; Baneyx, F. *Nat. Mater.* 2003, 2, 577-585.
8. Ahmad, G.; Dickerson, M. B.; Church, B. C.; Cai, Y.; Jones, S. E.; Naik, R. R.; King, J. S.; Summers, C. J.; Kroger, N.; Sandhage, K. H. *Adv. Mater.* 2006, 18, (13), 1759-1763.
9. Tomczak, M. M.; Slocik, J. M.; Stone, M. 0.; Naik, R. R. *Biochem. Soc. Trans.* 2007, 35, 512-515.
10. Ahmad, G.; Dickerson, M. B.; Cai, Y.; Jones, S. E.; Ernst, E. M.; Vernon, J. P.; Haluska, M. S.; Fang, Y.; Wang, J.; Subramanyam, G.; Naik, R. R.; Sandhage, K. H. *J. Am. Chem. Soc.* 2007, 130, (1), 4-5.
11. Dickerson, M. B.; Jones, S. E.; Cai, Y.; Ahmad, G.; Naik, R. R.; Kroger, N.; Sandhage, K. H. *Chem. Mater.* 2008, 20, (4), 1578-1584.
12. Matsui, H.; Gologan, B. *J. Phys. Chem. B* 2000, 104, (15), 3383-3386.
13. Djalali, R.; Samson, J.; Matsui, H. *J. Am. Chem. Soc.* 2004, 126, (25), 7935-7939.
14. Reches, M.; Gazit, E. *Nano Lett.* 2004, 4, (4), 581-585.
15. Reches, M.; Gazit, E. *Curr. Nanosci.* 2006, 2, (2), 105-111.
16. Scanlon, S.; Aggeli, A. *Nano Today* 2008, 3, (3-4), 22-30.
17. Cui, Y.; Wei, Q.; Park, H.; Lieber, C. M. *Science* 2001, 293, (5533), 1289-1292.
18. Law, M.; Greene, L. E.; Johnson, J. C.; Saykally, R.; Yang, P. *Nat. Mater.* 2005, 4, (6), 455-459.
19. Murphy, C. J.; Gole, A. M.; Hunyadi, S. E.; Orendorff, C. J. *Inorg. Chem.* 2006, 45, (19), 7544-7554.
20. Lauhon, L. J.; Gudiksen, M. S.; Wang, D.; Lieber, C. M. *Nature* 2002, 420, (6911), 57-61.
21. He, J. H.; Zhang, Y. Y.; Liu, J.; Moore, D.; Bao, G.; Wang, Z. L. *J. Phys. Chem. C* 2007, 111, (33), 12152-12156.
22. Yin, Y.; Lu, Y.; Sun, Y.; Xia, Y. *Nano Lett.* 2002, 2, (4), 427-430.
23. Dai, L.; Chen, X. L.; Zhang, X.; Zhou, T.; Hu, B. *Appl. Phys. A-Mater. Sci. Process.* 2004, 78, (4), 557-559.
24. Kun, H.; Yuanjian, Z.; Yunze, L.; Junhua, Y.; Dongxue, H.; Zhijuan, W.; Li, N.; Zhaojia, C. *Chem.-Eur. J.* 2006,12, (20), 5314-5319.
25. Cao, H. Q.; Xu, Z.; Sang, H.; Sheng, D.; Tie, C. Y. *Adv. Mater.* 2001, 13, (2), 121-123.
26. Reches, M.; Gazit, E. *Science* 2003, 300, (5619), 625-627.
27. Carny, O.; Shalev, D. E.; Gazit, E. *Nano Lett.* 2006, 6, (8), 1594-1597.
28. Chen, A.; Wang, H.; Li, X. *Chem. Comm.* 2005, (14), 1863-1864.
29. Gong, J.; Luo, L.; Yu, S.-H.; Qian, H.; Fei, L. *J. Mater. Chem.* 2006, 16, (1), 101-105.
30. Kroger, N.; Deutzmann, R.; Sumper, M. *Science* 1999, 286, (5442), 1129-1132.
31. Knecht, M. R.; Wright, D. W. *Chem. Comm.* 2003, (24), 3038-3039.
32. Gole, A.; Dash, C.; Ramakrishnan, V.; Sainkar, S. R.; Mandale, A. B.; Rao, M.; Sastry, M. *Langmuir* 2001, 17, (5), 1674-1679.
33. Felice, R. D.; Selloni, A.; Molinari, E. *J. Phys. Chem. B* 2003, 107, 1151-1156.
34. Obare, S. O.; Jana, N. R.; Murphy, C. J. *Nano Lett.* 2001, 1, (11), 601-603.

The invention claimed is:

1. A method for manufacturing a gold core, insulator shell nanostructure comprising:
(a) combining a silica-polymerizing peptide including a cysteine residual group with a surface of a gold nanostructure; and
(b) forming the gold core, insulator shell nanostructure by reacting the peptide combined with the surface of the gold nanostructure with a silica precursor represented by the following Formula $R_{1n}Si(OR_2)_{4-n}$ wherein each $R_1$ independently represents a hydrogen atom, a straight or branched alkyl group having 1 to 6 carbon atoms, a vinyl group or a phenyl group, each $R_2$ independently represents a straight or branched alkyl group having 1 to 6 carbon atoms, and n represents an integer of 0 to 3 wherein the silica-polymerizing peptide has the amino acid sequence:

SSKKSGSYSGSKGSKC.

2. The method of claim 1, wherein the gold nanostructure is selected from the group consisting of a gold nanoribbon, a gold nanoplatelet, a gold nanotube, a gold nanowire, a gold nanorod, a gold nanoparticle, a gold nanocage, a gold nanocomposite, a gold nanoflake, a gold nanoflower, a gold nanofoam, a gold nanomesh, a gold nanofiller, a gold nanopin film, a gold nanoring and a gold nanoshell.

3. The method of claim 1, wherein the step (B) is performed in a solution including the silica precursor.

* * * * *